United States Patent
Li et al.

(10) Patent No.: US 10,343,128 B2
(45) Date of Patent: Jul. 9, 2019

(54) REACTION-REGENERATION DEVICE AND PROCESS FOR ALKANE DEHYDROGENATION TO ALKENE

(71) Applicant: China University of Petroleum (East China), Qingdao, Shandong (CN)

(72) Inventors: Chunyi Li, Shandong (CN); Guowei Wang, Shandong (CN)

(73) Assignee: CHINA UNIVERSITY OF PETROLEUM (EAST CHINA), Qingdao (CN)

(*) Notice: Subject to any disclaimer, the term of this patent is extended or adjusted under 35 U.S.C. 154(b) by 0 days.

(21) Appl. No.: 16/239,643

(22) Filed: Jan. 4, 2019

(65) Prior Publication Data
US 2019/0134590 A1 May 9, 2019

Related U.S. Application Data

(63) Continuation of application No. 15/887,399, filed on Feb. 2, 2018.

(30) Foreign Application Priority Data

Apr. 1, 2017 (CN) .......................... 2017 1 0213552
Jun. 23, 2017 (CN) .......................... 2017 1 0485609
(Continued)

(51) Int. Cl.
*B01J 8/28* (2006.01)
*B01J 8/24* (2006.01)
(Continued)

(52) U.S. Cl.
CPC .............. *B01J 8/28* (2013.01); *B01J 8/0055* (2013.01); *B01J 8/0065* (2013.01); *B01J 8/24* (2013.01);
(Continued)

(58) Field of Classification Search
CPC ..... B01J 8/28; B01J 8/24; B01J 8/0055; B01J 8/0065; C07C 4/05; C07C 5/333; C10G 3/00
(Continued)

(56) References Cited

U.S. PATENT DOCUMENTS 4,038,038 A * 7/1977 Bunn, Jr. .................. B01J 8/24
    208/164
6,166,282 A 12/2000 Miller
(Continued)

FOREIGN PATENT DOCUMENTS

CN 102451677 A 5/2012
CN 105013412 A 11/2015
GB 844797 A * 8/1960 ................ B01J 8/28

*Primary Examiner* — Huy Tram Nguyen
(74) *Attorney, Agent, or Firm* — Buchanan Ingersoll & Rooney PC

(57) ABSTRACT

A reaction-regeneration device for catalytic dehydrogenation or/and catalytic cracking of alkanes comprises a reaction device and a regeneration device. The reaction device comprises a reactor and a disengager, and the disengager is located at an upper part of the reactor. The reactor comprises a tapering section, and diameters of cross sections of the tapering section gradually decrease from bottom to top. Secondary conversion of alkenes caused by back-mixing is reduced, and thus the yield and selectivity to alkenes are increased.

14 Claims, 8 Drawing Sheets

(30) Foreign Application Priority Data

Sep. 14, 2017 (CN) .......................... 2017 1 0827248
Sep. 14, 2017 (CN) .......................... 2017 1 0827786

(51) Int. Cl.
*C07C 4/06* (2006.01)
*C10G 3/00* (2006.01)
*C07C 5/333* (2006.01)
*B01J 8/00* (2006.01)

(52) U.S. Cl.
CPC ................ *C07C 4/06* (2013.01); *C07C 5/333* (2013.01); *C10G 3/00* (2013.01); *B01J 2208/00991* (2013.01)

(58) Field of Classification Search
USPC ........................................................ 422/141
See application file for complete search history.

(56) References Cited

U.S. PATENT DOCUMENTS

| | | |
|---|---|---|
| 7,396,971 B2 | 7/2008 | Smith et al. |
| 7,935,314 B2 | 5/2011 | Couch et al. |
| 8,692,045 B2 | 4/2014 | Qi et al. |
| 2007/0213573 A1 | 9/2007 | Ross et al. |
| 2011/0218373 A1 | 9/2011 | Qi et al. |
| 2015/0203763 A1 | 7/2015 | Brady et al. |
| 2015/0217252 A1 | 8/2015 | Bucci et al. |
| 2016/0016862 A1 | 1/2016 | Noyes |
| 2016/0030906 A1 | 2/2016 | Crnkovic et al. |
| 2016/0068454 A1 | 3/2016 | Nawaz et al. |
| 2016/0102033 A1 | 4/2016 | Yang et al. |

\* cited by examiner

REACTION-REGENERATION DEVICE AND PROCESS FOR ALKANE DEHYDROGENATION TO ALKENE

CROSS REFERENCE TO RELATED APPLICATIONS

This application is a continuation of U.S. patent application Ser. No. 15/887,399, filed on Feb. 2, 2018, entitled "REACTION-REGENERATION DEVICE AND PROCESS FOR ALKANE DEHYDROGENATION TO ALKENE," which claims priority to Chinese Patent Application No. 201710213552.4, filed Apr. 1, 2017, Chinese Patent Application No. 201710485609.6, filed Jun. 23, 2017, Chinese Patent Application No. 201710827786.8, filed Sep. 14, 2017, Chinese Patent Application No. 201710827248.9, filed Sep. 14, 2017, the disclosures of which are incorporated herein by reference in their entireties.

TECHNICAL FIELD

The present disclosure relates to circulating-fluidized-bed (FBD) reaction-regeneration devices, and particularly relates to a circulating-fluidized-bed reactor for alkane dehydrogenation reaction and a catalyst regenerator.

BACKGROUND

Alkenes and dialkenes (ethene, propene, butene, iso-butene, iso-prene, butadiene, etc.) are extensively applied to synthetic resin, plastics, high-octane-rating gasoline blending ingredients (methyl tert-butyl ether, methyl tert-amyl ether and alkylated oil) and other high additional value products. These alkenes are produced through the processes, such as hydrocarbon steam cracking (such as ethane steam cracking and naphtha steam cracking), alkene catalytic cracking (such as Superflex), heavy oil catalytic cracking (such as TMP and DCC) and heavy oil catalytic pyrolysis (such as CPP). And It is also an important technical route to prepare alkene and dialkene via the alkane catalyzed dehydrogenation.

As an important way for producing high-added-value low-carbon alkenes by reasonably using rich and low-carbon alkane resources, alkane dehydrogenation is increasingly taken into account by people.

Dehydrogenation of alkane is a relatively-strong endothermic reaction, for example, dehydrogenation of propane and iso-butane,

$C_3H_8 \rightarrow C_3H_6 + H_2 \quad \Delta H° = 124.3 \text{ kJ/mol}$

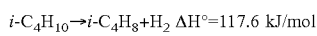

$i\text{-}C_4H_{10} \rightarrow i\text{-}C_4H_8 + H_2 \quad \Delta H° = 117.6 \text{ kJ/mol}$ Reaction heat of the dehydrogenation of the propane and reaction heat of the dehydrogenation of the iso-butane separately reach 124.3 kJ/mol and 117.6 kJ/mol at a temperature of 25° C. under a pressure of 0.1 MPa. The problems, such as what kind of reactor to be adopted and how to effectively supply heat to reactions, must be thought seriously.

Dehydrogenation reactions of alkanes are limited by thermodynamic equilibrium. Under the same temperature conditions, the larger molecules of alkanes are, the higher the equilibrium conversion ratio is; and for the same kind of alkanes, the higher the temperature is, the higher the equilibrium conversion ratio is. For ethane dehydrogenation to ethene, if a catalytic dehydrogenation method is adopted, the dehydrogenation is limited by the thermodynamic equilibrium, the conversion ratio per pass is too low. Thus, the dehydrogenation of the ethane adopts a steam pyrolysis technique at present, and the reaction is performed under high-temperature conditions with the temperature of 800° C. or above. For catalytic dehydrogenation of propane, butane, etc., the conversion ratio per pass and alkene selectivity are economically feasible under proper temperature conditions, so that a catalytic dehydrogenation method is generally adopted to prepare propene from propane, and butene or butadiene from butane.

In the aspect of catalytic dehydrogenation reactor, fixed bed, moving bed and circulating fluidized bed are all applied. Alkane dehydrogenation catalysts are liable to deactivation by coke formation, and Pt is liable to sintering in case of a Pt-based catalyst, thus the catalysts need frequent coke-burning regeneration or oxychlorination regeneration. As for a fixed bed, regeneration is inconvenient apparently; and in case of a moving bed and a fluidized bed, reaction and regeneration can be carried out continuously. The Pt-based catalyst is expensive, the fluidized bed can only employ Cr-based catalysts, and the Cr-based catalysts can cause serious pollution to environment. The moving bed adopts the Pt-based catalyst, and reaction is required to be carried out in the presence of hydrogen in order to guarantee that the catalyst has a regeneration period of several days. As a result, the conversion per pass will be lowered. And due to the lower conversion per pass and hydrogen circulation, the energy consumption of the moving beds can be very high.

In the aspect of catalyst regeneration, heat transfer efficiency and reaction efficiency, an optimal reactor for alkane dehydrogenation is a circulating fluidized bed obviously. Process flows performed in a circulating fluidized bed reactor are much simpler than those of the fixed beds and the moving beds, and the investment is lower in case of devices of the same scale. A focus of contradiction lies in the development of non-toxic and relatively-cheap catalysts capable of being applied to the fluidized bed and the mating of a circulating fluidized bed reactor according to properties and performance of the catalysts.

For a circulating fluidized bed reaction device for alkane dehydrogenation, a pursued objective in the field is to increase the conversion per pass and alkene selectivity forever. Whereas, in the reaction device, back-mixing phenomenon of gas phase is also one of factors affecting the selectivity and conversion for alkane dehydrogenation to alkene.

SUMMARY

An object of the present disclosure is to provide a reaction device for producing alkenes through catalytic dehydrogenation of alkanes or catalytic cracking of alkanes. The reaction device tapers in a fluid flowing direction, and thus, secondary conversion of alkenes caused by back-mixing is reduced.

Another object of the present disclosure is to provide a reaction device for producing alkenes through catalytic dehydrogenation of alkanes or catalytic cracking of alkanes. In the reaction section of the device, the reactant and catalysts are merged and flow upwards, so that the uniformity of temperature distribution in a reaction device can be effectively improved, and local high temperature is prevented.

Another object of the present disclosure is to provide a reaction device for producing alkenes through catalytic dehydrogenation-cracking of alkanes. In the reaction device dehydrogenation cracking is combined with catalytic dehydrogenation, so that total reaction temperature and catalyst regeneration temperature are greatly lowered. The reaction device tapers in the fluid flowing direction, and thus, secondary conversion of alkenes caused by back-mixing is reduced.

Another object of the present disclosure is to provide a regeneration device for an alkane dehydrogenation catalyst. The regeneration device facilitates full, rapid and safe combustion of fuels.

Another object of the present disclosure is to provide a regeneration device for an alkane dehydrogenation catalyst. The regeneration device facilitates heat exchange between the solid catalyst and high-temperature flue.

Another object of the present disclosure is to provide a regeneration device for an alkane dehydrogenation catalyst. Internal circulation of the catalyst is intensified, and the uniformity of temperature of the catalyst bed in the regeneration device is improved.

Another object of the present disclosure is to provide a method for producing alkenes through catalytic dehydrogenation of alkanes.

Another object of the present disclosure is to provide a method for producing alkenes through dehydrogenation and cracking of alkanes.

Another object of the present disclosure is to provide a regeneration method for an alkane dehydrogenation catalyst.

In one aspect, a reaction device for catalytic dehydrogenation or catalytic cracking of alkanes comprises a reactor and a disengager, the disengager being located above the reactor, wherein the reactor comprises a tapering section, and diameters of cross sections of the tapering section gradually decrease from bottom to top.

In some embodiments, the reactor further comprises a dense-phase section and a dilute-phase section, the dense-phase section is located below the tapering section, and the dilute-phase section is located above the tapering section.

According to the reaction device provided by the present disclosure, catalyst and reactant are merged and flow upwards in the tapering section. Diameters of cross sections of the tapering section gradually decrease in the flowing direction, so that secondary conversion caused by back-mixing of the product is reduced, heat of high-temperature catalysts can be fully utilized, thermal reactions caused by local high temperature are prevented, and thus, the selectivity to alkenes is improved.

In another aspect, a reaction device for producing alkenes through catalytic dehydrogenation-cracking of alkanes, comprises a catalytic dehydrogenation-cracking reactor and a disengager, the disengager being located above the reactor, wherein the reactor comprises a dense-phase dehydrogenation reaction section and a cracking reaction section, the cracking reaction section is located below the dense-phase dehydrogenation reaction section, and the diameter of a cross section of the cracking reaction section is smaller than that of the dense-phase dehydrogenation reaction section.

According to the catalytic dehydrogenation-cracking reaction device provided by the present disclosure, catalytic dehydrogenation and cracking of alkanes are integrated to be carried out in the same reactor, so that long-carbon-chain alkanes (such as n-butane, pentane or hexane) are converted into hydrogen and alkenes mainly including ethene and propene.

In another aspect, a catalyst regeneration device for alkane dehydrogenation comprises a regenerator for containing the catalyst and a regeneration disengager, diameters of cross sections of the regenerator gradually decreasing from top to bottom, the cross sections of the regenerator being circular.

The regeneration device for the alkane dehydrogenation catalyst, provided by the present disclosure, facilitates transfer of free radicals as well as rapid and full combustion of fuels, and thus operation safety of the device is guaranteed. Temperature distribution in the catalyst bed is uniform, catalyst sintering caused by too high local temperature is prevented, and the structure of the device is simplified.

DETAILED DESCRIPTION

Figure 1:
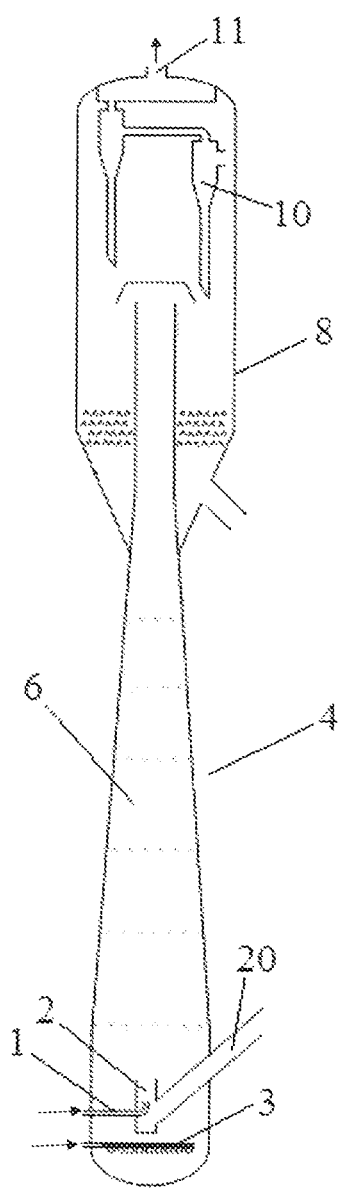
FIG. 1 shows an embodiment of a reaction device for producing alkenes through catalytic dehydrogenation or catalytic cracking of alkanes of the present disclosure.

The present disclosure is further described in detail below.

It is to be understood that the detailed description is not limited to specific methods unless otherwise specified, or to particular regents unless specified. It is also to be understood that the terminology used herein is for the purpose of describing particular aspects only, and is not intended to limit.

Definition

As used in the specification and the appended claims, dense-phase section means: a bed layer of this section is relatively large in diameter, relatively low in gas speed and relatively high in solid concentration. In the dense-phase section, the contact and reaction between two phases, i.e. a gas phase and a solid phase are facilitated.

As used in the specification and the appended claims, dilute-phase section means: a bed layer of this section is relatively small in diameter, relatively high in gas speed and relatively low in solid concentration. Objects of arranging the dilute-phase section comprises: linear speed is increased, to enable oil gas to rapidly leave a reactor and reduce secondary reactions of alkenes; the low solid concentration also facilitates reduction of secondary reactions, in particular production of coke; and the need of catalyst conveying is met.

The term "mass space-time" refers to a ratio of catalyst mass to hourly feeding mass.

The term "superficial gas velocity" refers to a velocity of fluid, escaping from materials of a bed layer, after the bed layer is fluidized. The superficial gas velocity is an important operation parameter of a circulating fluidized bed.

The term "oil gas" refers to a sum of all reactants and products in a reaction device of the present disclosure.

In the present disclosure, cracking raw material generally comprises alkanes having at least four carbon atoms (e.g., n-butane, pentane, hexane, etc.). Dehydrogenation raw material generally comprises iso-butane, propane and ethane.

As used herein, relational terms, such as "first", "second", "top", "bottom", "upper", "lower", "above", "below" etc. are for clarity and convenience in understanding the disclosure and accompanying drawing and do not connote or depend on any specific preference, orientation, or order, except where the context clearly indicates otherwise.

As used herein, the singular forms "a", "an", and "the" are intend to include the plural forms as well, unless the context clearly indicates otherwise. The term "and/or" includes any and all combination of one or more of the associated listed items.

DETAILED DESCRIPTION

In a first aspect, a reaction device for catalytic dehydrogenation or catalytic cracking of alkanes comprises a reactor and a disengager, the disengager being located above the reactor, wherein the reactor comprises a tapering section, and diameters of cross sections of the tapering section gradually decrease from bottom to top.

A catalyst riser is arranged inside the reactor, and an outlet end of the catalyst riser inside the reactor is located in a lower part of the reactor. Herein, the lower part of the reactor preferably means a space close to the bottom end of the reactor.

In a gas phase and solid phase flow-mixing reaction system, back-mixing, which is also called reverse mixing, is a mixing phenomenon. In a narrow sense, back-mixing means material mixing caused by movement opposite to a main flow direction in a continuous process. In a circulating-bed fluidized reaction process of catalytic dehydrogenation or catalytic cracking of alkanes, a back-mixing phenomenon of a gas phase is also an important factor affecting the selectivity to alkenes and conversion of alkanes. In the present disclosure, a catalyst outlet end is located in a lower part of the reactor. In the reactor, catalysts and reactants upward flow simultaneously, and a linear speed of gas in the reactor is gradually increased along with the tapered reaction section upwards, i.e., diameters of cross sections of the reaction section gradually decrease from bottom to top. In this way, reduction of the back-mixing phenomenon of the gas can be facilitated, secondary conversion of alkenes produced through dehydrogenation of alkanes is reduced, and selectivity to alkenes is improved.

In one embodiment, an outlet end of a regenerated catalyst conduit is connected with the catalyst riser. Preferably, the outlet end of the regenerated catalyst conduit is connected with a side wall of the catalyst riser.

In some embodiments, the regenerated catalyst conduit extends into the reactor, and the outlet end of the regenerated catalyst conduit is connected with the catalyst riser in the reactor.

The reaction device further comprises a feeding distributor, and the feeding distributor is located below the outlet end of the regenerated catalyst conduit in the reactor.

The reaction device further comprises a feeding distributor, and the feeding distributor is located below an outlet end of the catalyst riser in the reactor.

The regenerated catalyst conduit and the catalyst riser can be connected inside the reactor, and alternatively, can also be connected outside the reactor.

In the present disclosure, the regenerated catalyst conduit can be completely placed outside the reactor, and a catalyst enters into the reactor via the riser. The catalyst can enter the reactor from the bottom of the reactor via the riser. The catalyst can also directly enter the reactor from the side face of the reactor, or rises by the riser and then enters the reactor from the side face of the reactor, according to requirements of pressure equilibrium and spatial layout of the reactor and a regenerator.

In some embodiments, the catalyst riser extends into the reactor through the lower part of the reactor, and the regenerated catalyst conduit and the riser are connected outside the reactor.

In some embodiments, a rising medium pipe is also arranged in the catalyst riser for conveying a catalyst rising medium, one end of the rising medium pipe is located outside the reaction device, and the other end of the rising medium pipe is arranged in the catalyst riser.

In one embodiment, the reactor further comprises a dense-phase section and a dilute-phase section, the dense-phase section is located below the tapering section, and the dilute-phase section is located above the tapering section.

In some embodiments, diameters of cross sections of the tapering section gradually decrease from bottom to top, the dilute-phase section is connected with an upper end of the tapering section, the dense-phase section is connected with a lower end of the tapering section, and a lower end of the dense-phase section is a closed end. Preferably, both the dilute-phase section and the dense-phase section are equal-diameter pipes.

When the regenerated catalyst conduit is connected with the catalyst riser, a high-temperature regenerated catalyst firstly enters the catalyst riser in the reactor through the regenerated catalyst conduit. On one hand, by means of such arrangement, heat can be directly supplied to an endothermic alkane dehydrogenation reaction. This heat supply mode has the highest efficiency.

On the other hand, generally, if the high-temperature catalyst is in direct contact with oil gas, the defect, that the selectivity to alkenes is lowered due to local high temperature and serious thermal reactions, will be caused. However, in the present disclosure, pre-heated alkane raw material flows upwards from the bottom of the reactor together with the high-temperature catalyst sprayed out of the outlet of the riser, so that full contact and uniform mixing between the raw material and the catalyst are facilitated. It is also facilitated to utilize low-temperature feed and the strong endothermic effect of the dehydrogenation reaction to rapidly lower the temperature of the catalyst and prevent thermal reactions caused by local high temperatures, and thus, the selectivity to alkenes is improved. In addition, the high-temperature catalyst is sprayed into the dense-phase bed, and high solid concentration is beneficial to terminate transfer of free radicals and also is beneficial to reduce thermal reactions, and the alkene selectivity is improved.

In the present disclosure, there are a plurality of modes for the gradual decrease of diameters of cross sections of the reaction section from bottom to top, for example, the diameters of the cross sections of the reaction section continuously decrease; or from the lower end of the tapering section, the diameters of the cross sections of the reaction section firstly taper off, then, come into equal-diameter transition and then taper off, and so on alternately.

In some embodiments, the catalyst riser extends into the reactor from the bottom of the reactor or a side face of the lower part of the reactor. Preferably, the catalyst riser extends into the reactor from the bottom of the reactor and can be vertically and upwardly extended into the reactor from any position of the bottom. And most preferably, the catalyst riser and the reactor are arranged coaxially.

In some embodiments, the catalyst riser extended into the reactor from the bottom of the reactor, and the outlet of the catalyst riser is located below the dilute-phase section in the reactor. Preferably, the outlet of the catalyst riser is located below the tapering section of the reactor, i.e., the outlet of the catalyst riser is located in the dense-phase section of the reactor. More preferably, the height of the catalyst riser in the reactor does not exceed ⅔ the height of the dense-phase section.

In some embodiments, the catalyst riser and the regenerated catalyst conduit are formed in one piece.

In some embodiments, the tapering section of the reactor is in the shape of a conical frustum, and an included angle of a generatrix and an axis of the conical frustum is smaller than 89 degrees and optimally smaller than 45 degrees. The height of the tapering section is determined according to diameters of the dense-phase section and the dilute-phase section and the included angle of the generatrix and the axis of the tapering section. The size of the included angle of the generatrix and the axis of the conical frustum of the tapering section is more suitable for catalytic dehydrogenation of alkanes.

In some embodiments, the tapering section of the reactor is in the shape of a conical frustum, and an included angle of a generatrix and an axis of the conical frustum is smaller than 60 degrees and optimally smaller than 30 degrees. The height of the tapering section is determined according to diameters of the dense-phase section and the dilute-phase section and the included angle of the generatrix and the axis of the tapering section. The size of the included angle of the generatrix and the axis of the conical frustum of the tapering section is more suitable for catalytic cracking of alkanes.

A part of the dilute-phase section can extend into a disengager, and the other part of the dilute-phase section is located outside the disengager. The dilute-phase section can also completely extend into the disengager.

In some embodiments, the dilute-phase section of the reactor is connected with a cyclone separator in the disengager in an inserting manner. In this connection manner, the catalyst and oil gas can be rapidly separated, thus, reduction of secondary reactions of alkenes produced by dehydrogenation is facilitated, partial pressure of the oil gas in the disengager is also lowered, and a coking phenomenon in the disengager can be effectively prevented.

Herein, the inserting manner means that an outlet of the dilute-phase section is inserted into an inlet of the cyclone separator.

The height of a part, outside the disengager, of the dilute-phase section and the height of the catalyst riser outside the reactor are determined according to specific arrangement of the reactor and the regenerator. The specific arrangement of the reactor and the regenerator needs to be determined according to reaction conditions, regeneration conditions and a calculation result of pressure equilibrium of the reactor and the regenerator. Generally, the catalyst riser outside the reactor is required to be as short as possible, the position of the reactor is required to be as low as possible, thus a driving force that enables the catalyst to enter the reactor from the regenerator is increased, and a resisting force against the rising of the catalyst through the riser is reduced. The resisting force against the conveying catalyst is minimum in the device shown in FIG. 2 that the catalyst directly enters the dense-phase section of the reactor from the regenerated catalyst conduit. The length of h5 is determined by the pressure equilibrium of the reactor and the regenerator. Under the condition that structures and sizes of the reactor and the regenerator are definite, the length of h5 is basically definite and has no direct relationship with which variant is specifically adopted.

In some embodiments, both the catalyst riser and the rising medium pipe are equal-diameter pipes.

In some embodiments, the rising medium pipe extends into the riser through the bottom or side wall of the catalyst riser.

In some embodiments, an outlet end of the rising medium pipe is located at a position above the upper edge of a discharging opening of the regenerated catalyst conduit. Generally, the catalyst riser is placed vertically, and the regenerated catalyst conduit is connected with the side wall of the catalyst riser, so that the outlet end of the regenerated catalyst conduit is also an opening in the side wall of the catalyst riser.

Preferably, in an axial direction, the outlet end of the rising medium pipe is higher than the upper edge of the discharging opening of the regenerated catalyst conduit by a distance of no more than 0.1 m. More preferably, the outlet end of the rising medium pipe and the upper edge of the discharging opening of the regenerated catalyst conduit are located in the same horizontal plane.

In some embodiments, the cross sections of the reactor are circular, and the catalyst riser and the reactor are arranged coaxially.

The bottom of the catalyst riser can be closed and can also be in an open state. As long as a negative pressure is formed near the discharging opening of the regenerated catalyst conduit during upward running of a rising medium in the catalyst riser, the driving force enabling the catalyst to enter the reactor from the regenerator can be increased.

In some embodiments, the bottom of the catalyst riser is in a closed state.

According to the present disclosure, the catalyst riser is arranged inside the reactor, the regenerated catalyst conduit is connected with the catalyst riser, and a negative pressure is formed near the discharging opening of the regenerated catalyst conduit during upward running of a regenerated catalyst in the catalyst riser under the sucking and pushing of the rising medium. Thus, the driving force enabling the catalyst to enter the reactor from the regenerator is increased. In addition, the catalyst is sprayed out from an upper end opening of the riser at a high speed under the pushing of the rising medium, so that rapid mixing of a high-temperature catalyst and the catalyst in the reactor is facilitated, and it is prevented to form local high temperature in the bed layer. More preferably, in order to guarantee that the rising medium pipe plays good roles in sucking and pushing the catalyst, an outlet of the rising medium pipe can be located in the central axis of the catalyst riser.

The position of the outlet of the regenerated catalyst conduit is determined according to the angle of the regenerated catalyst conduit, the length of the catalyst riser and the position of the outlet of the catalyst riser. In the present disclosure, at a joint of the regenerated catalyst conduit and the catalyst riser, there is about 0.1 m to 2.0 m, optimally 0.3 m to 1.0 m, from the upper edge of the opening of the regenerated catalyst conduit on the catalyst riser to the outlet of the catalyst riser.

According to the reaction device provided by the present disclosure, in order to achieve the purpose of disengaging the catalyst by lowering a gas velocity, the diameter of the disengager is greater than that of the reactor.

In some embodiments, the feeding distributor is arranged below the catalyst riser in the reactor. A feeding system is close to the bottom of the reactor. Preferably, the feeding distributor comprises one or more annular pipes which are arranged on the same plane, and spray nozzles are arranged on the annular pipes.

The spray nozzles can face upwards or downwards, preferably face downwards.

In order to enable the catalyst and the feed to come into full contact and react in the reactor, grilles or porous distribution plates are arranged in the reactor and above the feeding distributor. Optimally, the distribution plates have a porosity of not greater than 50%.

In some embodiments, every two adjacent layers of grilles or porous distribution plates arranged in the reactor above the feeding distributor are spaced at a distance of 0.01 m to 2.0 m, preferably 0.1 m to 0.7 m. Through arranging the grilles or porous distribution plates, the distribution of gas and the catalyst is continuously changed, which promotes the full contact and reaction between the feed and the catalyst, and the gas-solid contact and reaction efficiency are increased.

An oil gas outlet is set in the top end of the reaction device, and a cyclone separator arranged in the disengager is connected with the oil gas outlet.

In the present disclosure, spent catalyst can be withdrawn from a side face, close to the bottom, of the disengager and enters the regenerator through the spent catalyst conduit. The spent catalyst can directly enter a dense-phase bed of a regenerator, or can also enter a disengager of the regeneration device. Preferably, the spent catalyst enters the disengager of the regeneration device. So the spent catalyst is in a dilute-phase fluidized state, and the rapid burning of coke is facilitated.

The reaction device for producing alkenes through dehydrogenation of alkanes, provided by the present disclosure, can be combined with a catalyst regenerator disclosed in the prior art to carry out circulating fluidized dehydrogenation reaction or catalytic cracking reaction.

In a second aspect, a catalyst regeneration device comprises a regenerator for containing catalyst and a regeneration disengager, and diameters of cross sections of the regenerator gradually decrease from top to bottom.

The cross sections of the regenerator are circular or quasi-circular.

It is known to one skilled in the art that the regeneration disengager is used for separating catalysts and fume from the regenerator after combustion reaction, and should be located above the regenerator.

In some embodiments, the appearance of the regenerator is in the shape of an inverted conical frustum, and cross sections of the conical frustum gradually decrease from top to bottom. Namely, the bottom of the regenerator has a small diameter, and the upper part of the regenerator has a big diameter.

According to the catalyst regeneration device provided by the present disclosure, air and fuel enter the regenerator from the bottom with a small diameter, the linear speed of the gas is high, and the fluidized density of the catalyst is low, so that the transfer of free radicals is facilitated. Thereby, the rapid and full combustion of the fuel is facilitated, and the operation safety of the device is guaranteed.

According to the catalyst regeneration device provided by the present disclosure, the regenerator is configured to be diameter-expanding from bottom to top, so that the linear speed in a central area is high, fluid flows upwards; the linear speed in a side wall area is low, the catalyst flows downwards. Thereby, an internal circulation that the catalyst flows upwards at the center and flows downwards at the side wall is formed. The bottom temperature of the regenerator is increased, and the successful initiation of the fuel is guaranteed, preventing potential safety hazards resulting from extinguishing. In addition, internal temperature distribution of a bed layer is uniform, and catalyst sintering caused by high local temperatures is prevented.

In addition, the diameter of the regenerator gradually expanded from bottom to top, and the linear speed of the gas gradually decreases from bottom to top, thus, the catalyst concentration with dilute-bottom and dense-top is formed. Low bottom catalyst concentration is beneficial to the full combustion of the fuel, and afterburning is prevented. High top catalyst concentration is beneficial to heat exchange between gas phase and solid phase. Temperature difference between a regeneration disengager and the upper part of a dense-phase section of the regenerator is reduced to the maximum. Thus, heat released from fuel combustion is sufficiently utilized.

According to the catalyst regeneration device provided by the present disclosure, a spent catalyst inlet which is used for connecting the regeneration disengager and a spent catalyst conduit is formed in the lower part of the regeneration disengager.

Alternatively, the spent catalyst inlet is formed in a dense-phase section of the upper part of the regenerator. Compared with a manner that the spent catalyst inlet is formed in the lower part of the regeneration disengager, spent catalyst directly enters a dense phase, which increases a resisting force to catalyst discharging and is unfavorable to coke combustion. If the spent catalyst inlet is formed in the lower part of the regeneration disengager, the catalyst is easy to be discharged, and coke combustion is facilitated.

Generally, diameters of upper and lower bottom faces of the regenerator are basically determined by three factors, i.e., linear speeds of an inlet and an outlet of a dense-phase section of the regenerator, the device scale and residence time (longer than 3 min generally) of the catalyst in the regenerator. The height of the regenerator is determined according to the height of the reactor and included angles (the included angle has certain design specifications and is 30 to 45 degrees generally) between the central axis and the generated catalyst conduit and between the central axis and the spent catalyst conduit. Thus, an included angle between the side face and the bottom surface or the central axis of the conical frustum is determined.

In one embodiment, a circular pipe sleeve is arranged at a lower position inside the regenerator and is coaxial with the regenerator.

In some embodiments, the height of the circular pipe sleeve in the regenerator does not exceed ⅔, optimally ⅓ the height of a dense-phase section of the catalyst.

In some embodiments, fuel and air are directly fed into the circular pipe sleeve.

The circular pipe sleeve is arranged at the bottom of the regenerator, air and fuel are directly sprayed into the circular pipe sleeve for combustion, and the catalyst flows downwards through an annular gap outside the sleeve. On one hand, full combustion of the fuel is facilitated. On the other hand, the catalyst can smoothly enter a gas stripping section of the regenerator in the condition of high linear speed of the bottom of the regenerator, and the circulation of the catalyst between the reactor and the regenerator is not affected.

In the present disclosure, the term "circular pipe sleeve" can be understood as a cylindrical pipe.

As a catalyst regeneration device in the prior art, the regeneration disengager is arranged above the regenerator, the gas stripping section is arranged below the regenerator, a cyclone separator is arranged in the regeneration disengager, and a flue outlet is formed in the top of the regeneration disengager. Several layers of grilles or distribution plates are arranged in the regenerator.

In a third aspect, a reaction device for producing alkenes through catalytic dehydrogenation-cracking of alkanes, comprises a catalytic dehydrogenation-cracking reactor and a disengager, and the disengager is located above the reactor. The reactor comprises a dehydrogenation dense-phase reaction section and a cracking reaction section, the cracking reaction section is located below the dehydrogenation dense-phase reaction section, and the diameter of a cross section of the cracking reaction section is smaller than that of the dehydrogenation dense-phase reaction section.

In some embodiments, the reactor further comprises a tapering section, the tapering section is located above the dehydrogenation dense-phase reaction section, and diameters of cross sections of the tapering section gradually decrease from bottom to top.

In the aspect of alkane dehydrogenation, for the production of mono-alkenes through dehydrogenation of heavy alkanes, such as n-butane, pentane and hexane, the conversion per pass is not high and does not exceed 50% generally. Besides, the formed alkenes can not be separated from the alkanes by simple reaction or rectification, and they should be separated from the alkanes by extraction method, and the energy consumption of separation is high. The mono-alkenes are less used in the chemical industry, and need to be further cracked to high valued ethene and propene. With the combination of catalytic dehydrogenation and cracking, cracking feed, i.e., heavy alkanes can be converted into high valued ethene and propene.

On the other hand, in a case of catalytic cracking reaction, the reaction temperature is relatively high, and the lifetime of the catalyst is relatively short. If the catalytic dehydrogenation and cracking reactions are combined, under the condition of same cracking feeding rate and reaction temperature, due to the introduction of dehydrogenation feed, the circulation amount of the catalyst is increased, the regeneration temperature for the catalyst is lowered. Thus, it is facilitated to prolong the lifetime of the catalyst. The dehydrogenation reaction is performed at low temperature, so the temperature of oil gas leaving the reactor is lower than that of oil gas of single cracking by about 100° C., and thus, the possibility of subsequent alkene coking can be effectively lowered.

A feeding annular pipe for cracking the feed is arranged at a lower position inside the cracking reaction section, and a feeding annular pipe for dehydrogenation of the feed is arranged at a lower position inside the dehydrogenation dense-phase section.

In one embodiment, a catalyst riser extends into the cracking reaction section from the lower part of the cracking reaction section, and a regenerated catalyst conduit and the catalyst riser are connected outside the cracking reaction section.

In one embodiment, the reaction device further comprises a dilute-phase section, and the dilute-phase section is located above the tapering section.

In the present disclosure, diameters of cross sections of the tapering section gradually decrease from bottom to top. The dilute-phase section is connected with the upper end of the tapering section. The dehydrogenation dense-phase section is connected with the lower end of the tapering section, the other end of the dehydrogenation dense-phase section is connected with the cracking reaction section, and the lower end of the cracking reaction section is a closed end. Preferably, the dilute-phase section, the dehydrogenation dense-phase section and the cracking reaction section are equal-diameter pipes.

According to the reaction device for producing alkenes through catalytic dehydrogenation-cracking of alkanes, provided by the present disclosure, the arrangement of other components and mutual relationships thereof can employ all embodiments of the reaction device for the catalytic dehydrogenation or catalytic cracking of alkanes, provided by the present disclosure, for example position relationships among the catalyst riser, the rising medium pipe and the regenerated catalyst conduit and arrangement of the tapering section.

The catalyst regeneration device provided by the present disclosure can be used in combination with the reaction device for producing alkenes through catalytic dehydrogenation-cracking of alkanes, or the reaction device for the catalytic dehydrogenation or catalytic cracking of alkanes provided by the present disclosure.

In a fourth aspect, a preparation method for producing alkenes through dehydrogenation of alkanes comprises the following steps: feed enters a reactor from a feeding distributor, the feed and catalyst are merged and flow upwards, and the feed and the catalyst come into contact and are subjected to catalytic reactions. At an intersecting horizontal plane of the lower end of a disengager and a reactor, an average linear speed of gas is in a range from 0.3 m/s to 10.0 m/s, a reaction temperature is optimally in a range from 500° C. to 650° C., and a mass space-time of the reaction is in a range from 0.1 h to 15 h.

In another aspect, at a cross section of an outlet of a catalyst riser in the reaction section, an average linear speed of the gas is in a range from 0.01 m/s to 3 m/s, optimally from 0.2 m/s to 0.7 m/s. In the tapering section of the reactor, the linear speed of gas in the reactor is gradually increased, and thus, the reduction of back-mixing of the gas is facilitated.

In some embodiments, the reaction temperature is in a range from 550° C. to 620° C.

In the present disclosure, a reaction temperature inside the reactor is the average temperature. A method for measuring the average temperature is as follows: 5 to 10 temperature measuring points are set at uncoaxial radial positions in the reactor, and an average value of the temperatures of the temperature measuring points is the reaction temperature inside the reactor.

In some embodiments, the mass space-time of the reaction is in a range from 1 h to 8 h.

A pressure of the top of a disengager of the reaction device is in a range from −0.01 MPa to 0.1 MPa, optimally from 0 MPa to 0.05 MPa (gauge pressure).

In some embodiments, a superficial gas velocity in a catalyst riser is in a range from 0.5 m/s to 20 m/s, preferably 3 m/s to 10 m/s.

In some embodiments, at an outlet of a rising medium pipe, a linear speed of a rising medium is in a range from 5 m/s to 50 m/s, preferably 15 m/s to 30 m/s.

In the present disclosure, the rising medium is selected from dehydrogenation feed, water vapor, nitrogen, hydrogen, dry gas or other light hydrocarbons, etc., optimally dehydrogenation feed or nitrogen.

In a fifth aspect, a preparation method for producing alkenes through catalytic cracking of alkanes comprises the following steps: feed enters a reactor from a feeding distributor, the feed and catalyst are merged and flow upwards, and the feed and the catalyst come into contact and are subjected to catalytic reactions. In a dense-phase section, an average temperature is in a range from 630° C. to 800° C., preferably 680° C. to 730° C.; and an average residence time of oil gas in a reactor does not exceed 30 s, preferably not exceed 10 s.

In some embodiments, in a dense-phase section for a catalytic cracking reaction, a superficial gas velocity of the oil gas is in a range from 0.3 m/s to 10 m/s, optimally 0.5 m/s to 5 m/s.

A reaction temperature of the catalytic cracking is maintained through regulating preheating temperature of feed and temperature and circulation of regenerated catalyst. A reaction pressure (by hydrocarbon partial pressure) is not higher than 0.3 MPa (gauge pressure), optimally not higher than 0.05 MPa.

In the present disclosure, both the cracking reaction and the catalytic dehydrogenation use the same catalyst, i.e., a non-noble-metal dehydrogenation catalyst, for example, a non-noble-metal and environment-friendly dehydrogenation catalyst disclosed in a Chinese patent ZL 201110123675.1. Therefore, catalytic cracking means that alkanes are subjected to cracking reactions in the presence of dehydrogenation catalyst under high-temperature conditions.

In the present disclosure, the rising medium is selected from dehydrogenation feed, water vapor, nitrogen, hydrogen, dry gas or other light hydrocarbons, etc., preferably the rising medium comprises water vapor. By using water vapor, the gas stripping effect is better than that of using nitrogen. Water vapor is condensed into water before entering a gas compressor and does not enter a subsequent compression and separation process. In a case of nitrogen gas-stripping, nitrogen participates in the entire compression and separation process, including a PSA hydrogen gas separation process. Thus, the investment of equipment and energy consumption of the entire process will be increased, and the calorific value of dry gas will be reduced. Therefore, through carrying out gas stripping on a spent catalyst by adopting water vapor instead of dry gas, the investment and operating cost of the device is reduced.

In a sixth aspect, a preparation method for producing alkenes through catalytic dehydrogenation-cracking of alkanes comprises the following steps: alkanes enter a cracking reaction section and are subjected to catalytic cracking reaction, an average temperature inside the cracking reaction section is in a range from 630° C. to 800° C., an average residence time of oil gas in the cracking reaction section does not exceed 30 s, and then, the cracking reaction product enters a dehydrogenation dense-phase reaction section;

in the dehydrogenation dense-phase reaction section, alkanes are fed through a feeding annular pipe, a mixture of the alkanes and the cracking reaction product is subjected to a catalytic dehydrogenation reaction in the dehydrogenation dense-phase reaction section, an average temperature of the dehydrogenation dense-phase reaction section is controlled to 550° C. to 650° C., and an average residence time of oil gas in the dehydrogenation dense-phase reaction section does not exceed 50 s; and product of the dehydrogenation dense-phase reaction section enters a tapering section and then is subjected to subsequent separation, thereby obtaining dehydrogenation product.

In some embodiments, the reaction temperature is in a range from 680° C. to 730° C. in the cracking reaction section.

In some embodiments, in the cracking reaction section, a superficial gas velocity of gas is in a range from 0.3 m/s to 10 m/s, preferably 0.5 m/s to 5.0 m/s.

In some embodiments, an average residence time of oil gas in the cracking area does not exceed 10 s in the cracking reaction section.

In some embodiments, the reaction temperature is in a range from 580° C. to 610° C. in the dehydrogenation dense-phase section.

In some embodiments, a superficial gas velocity of gas is in a range from 0.1 m/s to 5.0 m/s, preferably 0.5 m/s to 1.5 m/s in the dehydrogenation dense-phase section.

In some embodiments, an average residence time of oil gas in the cracking area does not exceed 20 s in the cracking reaction section.

According to the preparation method for producing alkenes through catalytic dehydrogenation-cracking of alkanes, provided by the present disclosure, oil gas obtained after the cracking reaction directly enters the dehydrogenation dense-phase section, and dehydrogenation feed (such as propane and ethane) is additionally fed into the dehydrogenation dense-phase section. The feeding for dehydrogenation results in increasing the circulation of the catalyst, and regeneration temperature of the catalyst is lower than temperature of cracking reaction section. Due to the lowering of the catalyst regeneration temperature, the lifetime of the catalyst is prolonged, and the occurrence of coking phenomenon during subsequent alkene treatment is lowered.

In the present disclosure, the rising medium is consistent with that in catalytic cracking reaction.

In a seventh aspect, a regeneration method for alkane dehydrogenation catalyst, provided by the present disclosure, comprises the steps: spent catalyst enters a regeneration disengager, and fuel and air enter a regenerator from the lower part or bottom of the regenerator;

the gas moves upwards in the regenerator, the linear speed of the gas gradually decreases from bottom to top, and, the catalyst moves upwards at a central area and moves downwards at a side wall area in the regenerator so as to form an internal circulation; and the regenerated catalyst leaves the regenerator through a regenerated catalyst conduit, and the flue resulting from a combustion reaction is discharged from a flue outlet in the top of the regeneration disengager.

According to the catalyst regeneration method provided by the present disclosure, the linear speed of a central area of the regenerator is high, and the catalyst flows upwards. The linear speed at the side wall area is low, and the catalyst flows downwards. An internal circulation that the catalyst flows upwards at the center and flows downwards at the side wall is formed, so that the bottom temperature of the regenerator is increased, the successful initiation of the fuel is guaranteed, and potential safety hazards resulting from extinguishing is prevented; and the temperature distribution inside a bed layer is uniform, and catalyst sintering caused by high local temperatures is prevented. The linear speed gradually decreases from bottom to top, and thus, the catalyst is distributed into dilute density in the bottom and dense density in the top. Thereby, afterburning is prevented. High catalyst concentration in the top is beneficial to heat exchange between a gas phase and a solid phase, temperature difference between a disengager and the upper part of a dense-phase fluidized section of the regenerator is reduced to the maximum, and thus, heat released from fuel combustion is sufficiently utilized.

In one embodiment, a superficial gas velocity of a bottom fuel inlet of a catalyst dense-phase bed layer of the regenerator is in a range from 0.1 m/s to 3 m/s under actual operating conditions, optimally a range from 0.3 m/s to 2 m/s.

The superficial gas velocity of the bottom fuel inlet of the catalyst dense-phase bed layer of the regenerator refers to a superficial gas velocity under the condition that the lower part of the regenerator is free of a circular pipe sleeve.

The bottom fuel inlet of the catalyst dense-phase bed layer of the regenerator is an inlet of fuel and air. At the inlet, the linear speed is high, and the catalyst concentration is relatively low.

In some embodiments, a superficial gas velocity in the top of the dense-phase bed layer of the regenerator is in a range from 0.01 m/s to 1 m/s properly, optimally a range from 0.05 m/s to 0.5 m/s.

In some embodiments, the circular pipe sleeve is arranged in the lower part of the regenerator, and a superficial gas velocity inside the circular pipe sleeve is in a range from 1 m/s to 30 m/s, preferably in a range from 3 m/s to 5 m/s. A superficial gas velocity of gas at this position is determined according to actual operating requirements or conditions.

The temperature inside the regenerator is 600° C. to 850° C., preferably 630° C. to 750° C.

The fuel is selected from a gas fuel, and alternatively is selected from a liquid fuel free of sulfur and metals.

In the present disclosure, the term "dense-phase bed layer of regenerator" is a frequently-used term in the field of chemical industry, is also called a dense-phase fluidized section, is a primary area for a catalyst regeneration reaction and corresponds to a dilute-phase fluidized section. Specifically, in the present disclosure, the dense-phase bed layer of the regenerator means an internal space of the regenerator.

The present disclosure is further described with reference to the drawings:

Embodiment 1

Figure 2:
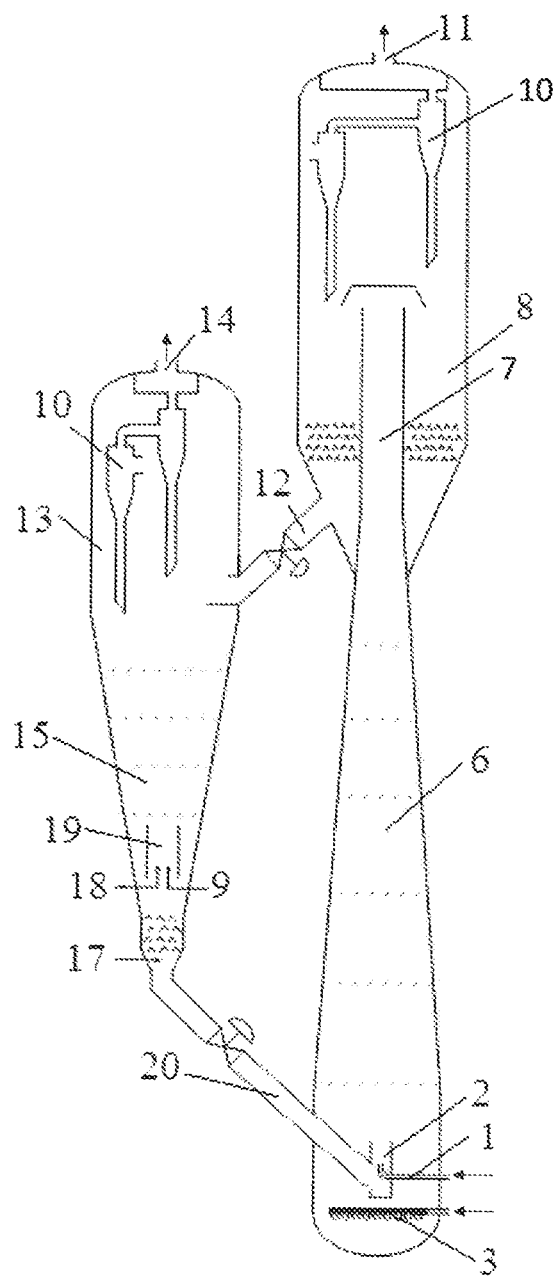
FIG. 2 shows an embodiment of a reaction-regeneration device for producing alkenes through catalytic dehydrogenation or catalytic cracking of alkanes of the present disclosure.

As shown in FIG. 1 and FIG. 2, a reaction device for catalytic dehydrogenation of alkanes is combined with a catalyst regeneration device, provided by the present disclosure. The two devices can be used separately and used in combination with other reaction devices or catalyst regeneration devices in the prior art respectively.

The reaction device for catalytic dehydrogenation of alkanes as shown in FIG. 1 comprises a reactor 4 and a disengager 8, the disengager 8 is located above the reactor 4. The reactor 4 comprises a tapering section 6, the tapering section 6 tapers from bottom to top. A regenerated catalyst conduit 20 extends into the tapering section 6, and an outlet of the regenerated catalyst conduit 20 is located in a lower part of the tapering section 6.

A catalyst riser 2 is arranged in a lower position inside the tapering section 6. In the tapering section 6, the regenerated catalyst conduit 20 is connected with the catalyst riser 2 inside the tapering section. A rising medium pipe 1 for conveying a rising medium is arranged in the catalyst riser 2. The bottom of the catalyst riser 2 is closed, and the rising medium pipe 1 extends into the riser 2 through the bottom or side wall of the catalyst riser 2. An outlet end of the rising medium pipe 1 and the upper edge of a discharging opening of the regenerated catalyst conduit 20 are located in the same horizontal plane. Thus, a negative pressure is formed nearby the discharging opening of the regenerated catalyst conduit during continuous upward running of the rising medium in the rising medium pipe, and a driving force enabling a catalyst to enter the reactor from a regenerator is increased.

In this embodiment, cross sections of the reactor 4 are all circular, and both the catalyst riser and the rising medium pipe in the catalyst riser are arranged coaxial with the reactor 4.

In the tapering section 6, a feeding annular pipe 3 is arranged below the catalyst riser 2, and a spray nozzle is arranged on the annular pipe and faces downwards. Grilles or porous distribution plates are arranged above the feeding annular pipe 3 in the tapering section 6.

An oil gas outlet 11 is formed in the top end of the reaction device, and a cyclone separator 10 is arranged in the disengager 8 and is connected with the oil gas outlet 11. The reactor 4 further comprises a dilute-phase section 7 which is located above the tapering section 6, and the reactor partially extends into the disengager 8.

Figure 8:
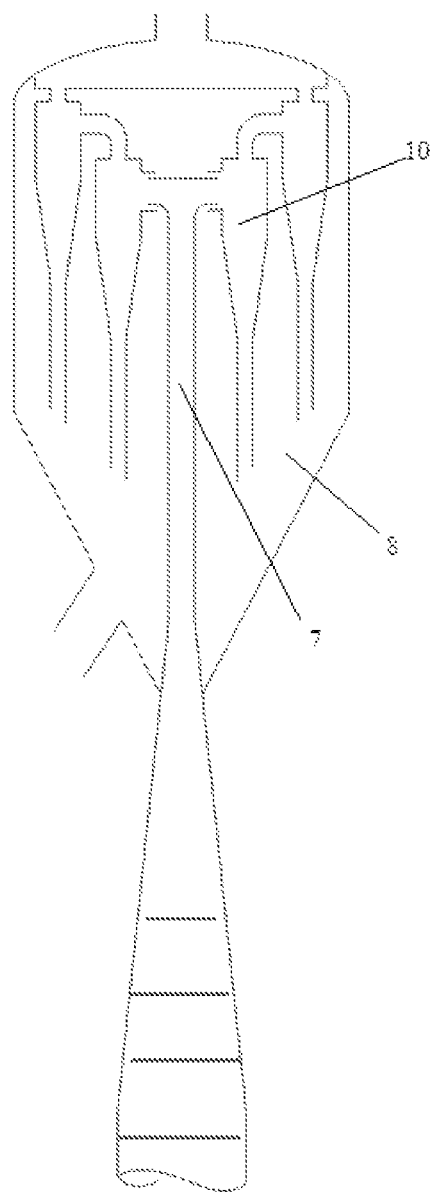
FIG. 8 shows a connection mode of a reactor and a disengager of the present disclosure.

The dilute-phase section of the reactor is connected with the separator 10 in a inserted manner, referring to FIG. 8. At the tail end of the dilute-phase section is provided with three-way pipe, and an outlet of the three-way pipe is inserted into an inlet of the separator without contact with each other. Namely, there is an aperture between the pipe inserted into the separator and the side wall of the inlet of the separator.

The regenerated catalyst conduit 20 is connected with the bottom of the catalyst regenerator 15 of the regeneration device. A first end of a spent catalyst conduit 12 is connected with a side wall, close to the bottom, of a reactor disengager 8, and a second end of the spent catalyst conduit 12 is connected with a regeneration disengager 13 of the regeneration device. The regeneration disengager 13 of the regeneration device is located above the regenerator 15. The regenerator 15 tapers from top to bottom and is in the shape of an inverted conical frustum.

Figure 3:
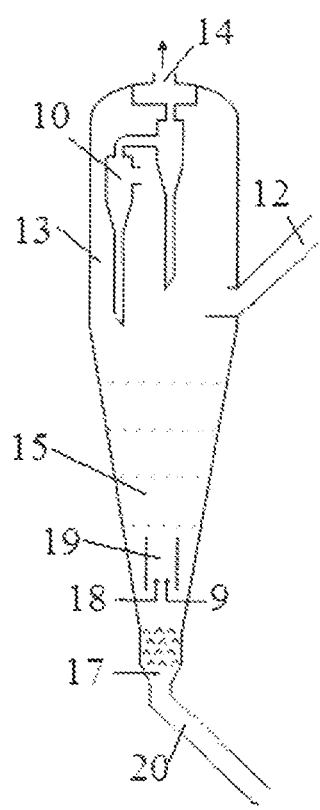
FIG. 3 shows an embodiment of a catalyst regeneration device of the present disclosure.

The catalyst regeneration device as shown in FIG. 3 further comprises a gas stripping section 17 which is located below the regenerator. A spent catalyst inlet which is used for communicating the regeneration disengager 13 and the spent catalyst conduit 12 is formed in the lower part of the regeneration disengager 13, and a circular pipe sleeve 19 is arranged at the bottom of the regenerator 15. A spent catalyst enters the regeneration disengager 13 from the spent catalyst conduit 12, and fuel 9 and air 18 enter the circular pipe sleeve 19 from the bottom of the regenerator. A superficial gas velocity in the circular pipe sleeve is in a range from 1 m/s to 30 m/s, optimally 3 m/s to 5 m/s. The catalyst is subjected to combustion regeneration in the regenerator at a temperature of 600° C. to 850° C., preferably 630° C. to 750° C. The regenerated catalyst enters the alkane dehydrogenation reactor for reuse through the regenerated catalyst conduit 20 to achieve continuous reaction-regeneration reaction. The catalyst and flue, entering the regeneration disengager after combustion, are separated by the cyclone separator 10, and the flue is discharged from a flue outlet 14.

Embodiment 2

Figure 4:
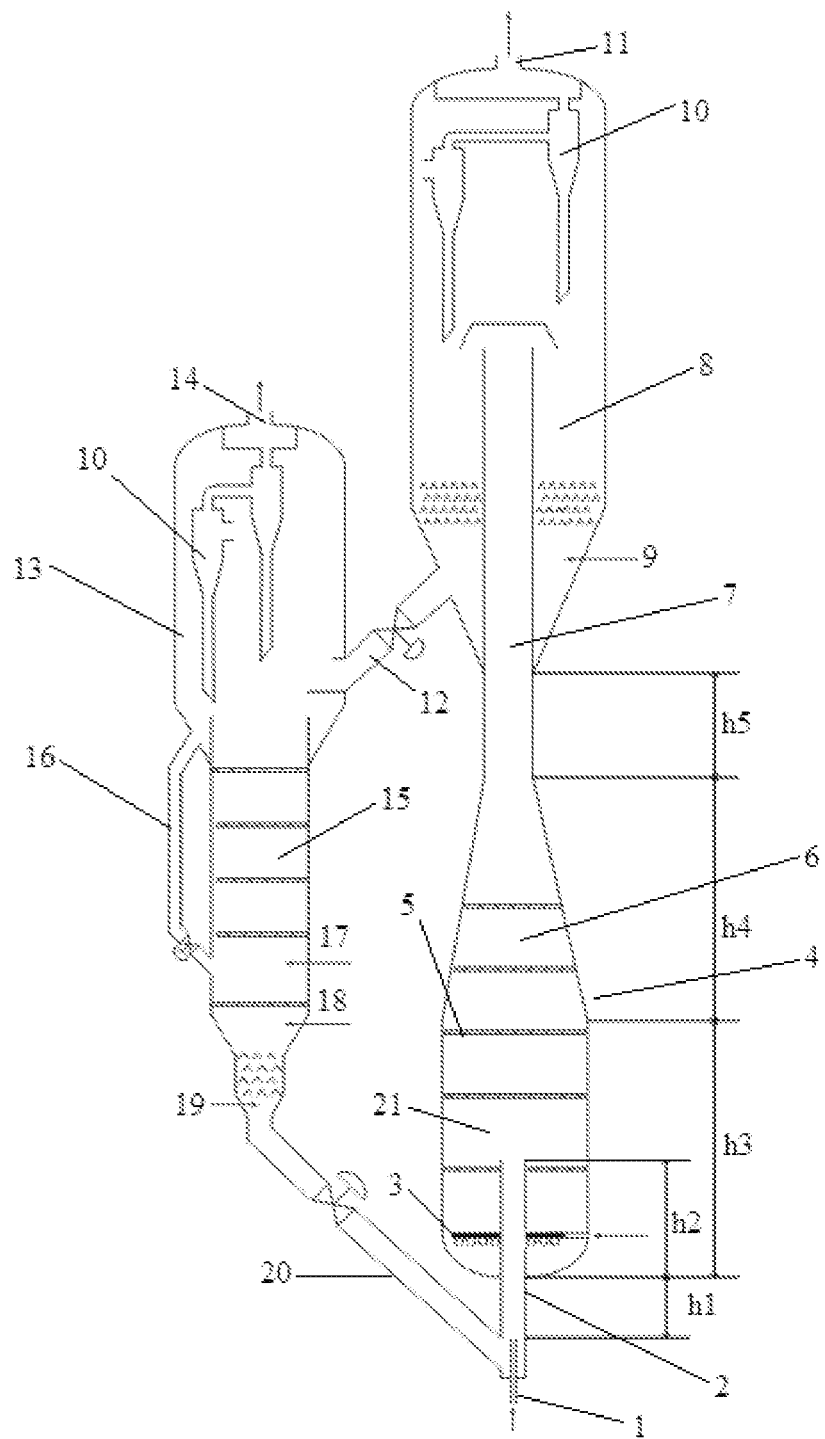
FIG. 4 shows another embodiment of a reaction-regeneration device for producing alkenes through catalytic dehydrogenation or catalytic cracking of alkanes of the prevent disclosure.

Referring to FIG. 4, a reaction device for producing alkenes through catalytic dehydrogenation or catalytic cracking of alkanes is provided by the present disclosure. Except that a reactor structure and a mode of connection between a catalyst riser and a regenerated catalyst conduit are different, other structures and relationships of connection refer to the embodiment 1.

The reaction device for producing alkenes through catalytic dehydrogenation or catalytic cracking of alkanes comprises a reactor 4 and a disengager 8, and the disengager 8 is located above the reactor 4. A reactor 4 comprises a dilute-phase section 7, a tapering section 6 and a dense-phase section 21, the dense-phase section 21 is located below the tapering section 6, and the dilute-phase section 7 is located above the tapering section 6. Diameters of cross sections of the tapering section 6 gradually decrease from bottom to top. A catalyst riser 2 extends into the reactor 4 from a lower part of the reactor 4, and a regenerated catalyst conduit 20 is connected with the catalyst riser 2 outside the reactor 4.

The height h2 of the catalyst riser in the dense-phase section does not exceed ⅔ the height h3 of the dense-phase section. The tapering section 6 of the reactor is a transition section of the dense-phase section 21 and the dilute-phase section 7. An included angle between a generatrix and an axis of the tapering section is smaller than 89°, optimally smaller than 45°. The height h4 of the tapering section is determined according to the diameter of the dense-phase section, the diameter of the dilute-phase section and the included angle between the generatrix and the axis of the tapering section.

The catalyst riser 2 extends into the dense-phase section 21 of the reactor 4 from the center of the bottom of the reactor 4. A rising medium pipe 1 extends into the riser 2 through the bottom of the catalyst riser 2. The regenerated catalyst conduit 20 and the catalyst riser 2 are connected outside the reactor 4, and an outlet end of the rising medium pipe is higher than an upper edge of a discharging opening of the regenerated catalyst conduit by a distance of no more than 0.1 m.

Cross sections of all sections of the reactor 4 are circular, and both a cross section of the catalyst riser and a cross section of the rising medium pipe are circular. The catalyst riser 2, the reactor 4 and the disengager 8 are all coaxially arranged.

A feeding annular pipe 3 is arranged in the dense-phase section 21 of the reactor 4, and grilles or porous distribution plates are arranged above the feeding annular pipe 3 in the dense-phase section and the tapering section of the reactor 4.

Embodiment 3

Figure 5:
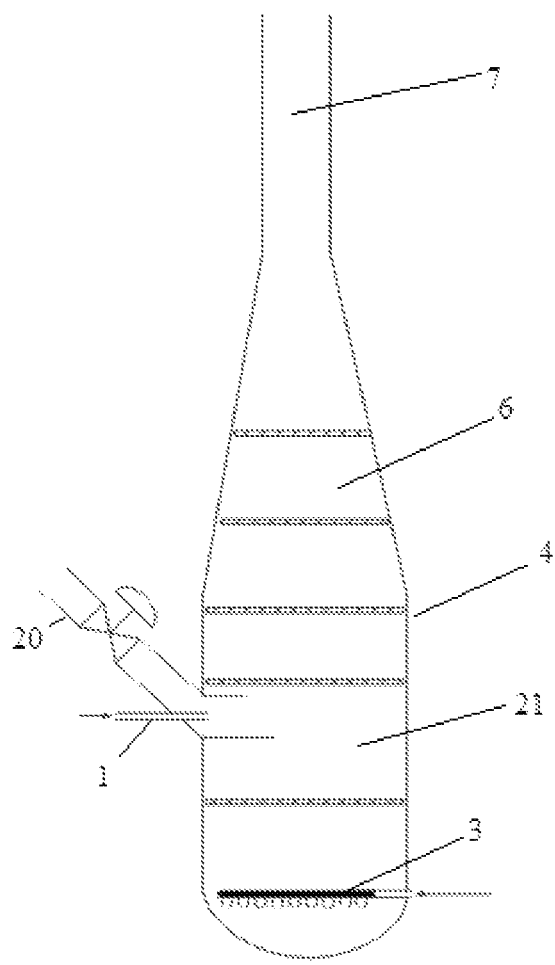
FIG. 5 shows a second embodiment of a reaction device for producing alkenes through catalytic dehydrogenation or catalytic cracking of alkanes of the present disclosure.

Referring to FIG. 5, compared with the embodiment 2, this embodiment has a different catalyst riser arrangement mode. In this embodiment, a regenerated catalyst conduit 20 extends into a reactor 4 from a side face of a dense-phase section 21, and a rising medium pipe 1 is inserted into the regenerated catalyst conduit 20 in the reactor 4.

Figure 6:
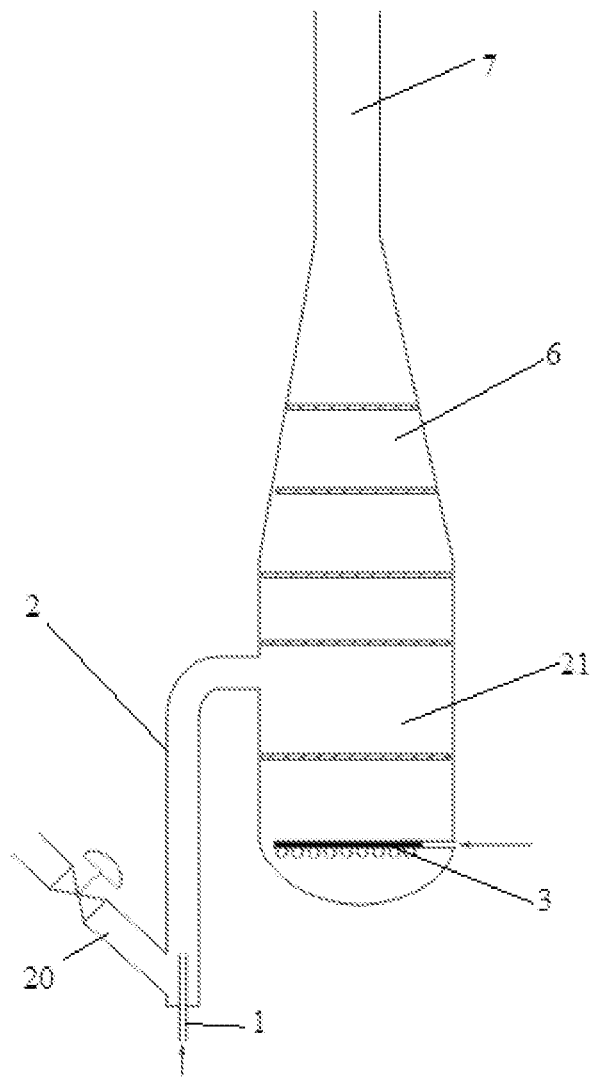
FIG. 6 shows a third embodiment of a reaction device for producing alkenes through catalytic dehydrogenation or catalytic cracking of alkanes of the present disclosure.

Referring to FIG. 6, the arrangement of catalyst riser in the embodiment is different from that of the embodiment 2. A catalyst riser 2 is arranged outside the reactor 4, one end of the catalyst riser 2 is connected with a side of the dense-phase section 21 and communicates with the dense-phase section 21, and the regenerated catalyst conduit is connected with the catalyst riser. The rising medium pipe 1 extends into the catalyst riser 2 from the other end of the catalyst riser 2. An outlet end of the rising medium pipe 1 is higher than an upper edge of a discharging opening of the regenerated catalyst conduit by a distance of no more than 0.1 m. More preferably, the outlet end of the rising medium pipe and the upper edge of the discharging opening of the regenerated catalyst conduit are located in the same horizontal plane.

Embodiment 4

Figure 7:
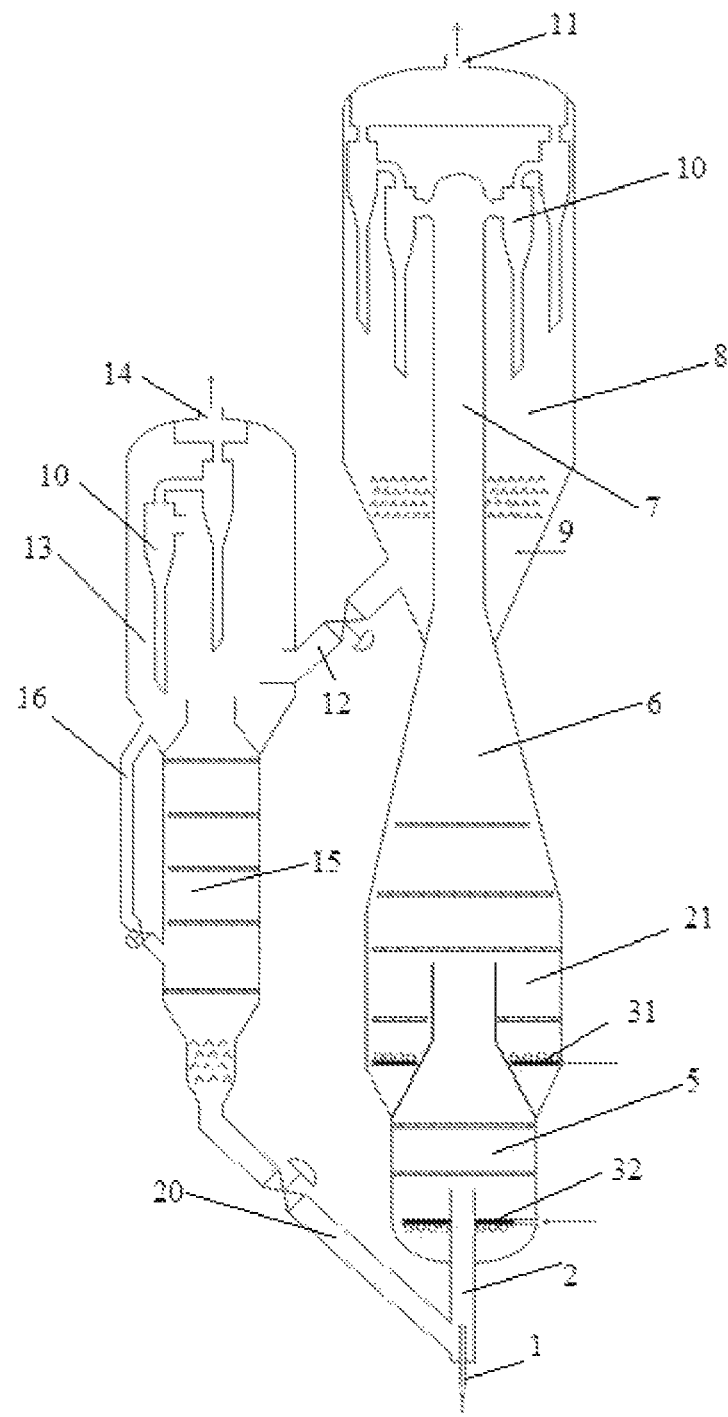
FIG. 7 shows an embodiment of a reaction device-regeneration device combination for producing alkenes through catalytic dehydrogenation—cracking of alkanes of the present disclosure.

Referring to FIG. 7, a reaction device for producing alkenes through catalytic dehydrogenation-cracking of alkanes comprises a catalytic dehydrogenation-cracking reactor and a disengager 8, and the disengager 8 is located above the reactor 4. Wherein, the reactor comprises a tapering section 6, a dehydrogenation dense-phase section 21 and a cracking reaction section 5. The tapering section 6 is located above the dehydrogenation dense-phase section 21, and the cracking reaction section 5 is located below the dehydrogenation dense-phase section 21. The tapering section 6 tapers from bottom to top. The diameter of a cross section of the cracking reaction section 5 is smaller than that of the dehydrogenation dense-phase section 21.

A feeding annular pipe 31 for dehydrogenation of the feed is arranged in a lower part of the dehydrogenation dense-phase section 21, and a feeding annular pipe 32 for catalytic cracking of the feed is arranged in a lower part of the cracking reaction section 5.

A catalyst riser 2 extends into the reactor from the lower part of the cracking reaction section 5, and a regenerated catalyst conduit 20 is connected with the catalyst riser 2 outside the reactor. A rising medium pipe 1 extends into the catalyst riser 2 through the bottom of the catalyst riser 2.

The regenerated catalyst conduit 20 is connected with the bottom of a catalyst regenerator 15 of a regeneration device. A first end of a spent catalyst conduit 12 is connected with a side wall, close to the bottom, of a disengager 8, and a second end of the spent catalyst conduit 12 is connected with a catalyst regeneration disengager 13 of the regeneration device. A regeneration disengager 13 of the regeneration device is located above the regenerator 15.

An external circulating pipe 16 is arranged outside the regeneration disengager 13 and the catalyst regenerator 15, one end of the external circulating pipe 16 is connected with the lower side part of the catalyst regenerator 15, and the other end of the external circulating pipe 16 is connected with the lower side part of the regeneration disengager 13.

A flue outlet 14 is formed in the top of the regeneration disengager 13. A cyclone separator 10 is arranged in the regeneration disengager 13 and is connected with the flue outlet 14.

Other components in the reactor and arrangement modes refer to the embodiment 2.

Embodiment 5

A reaction-regeneration reaction device for catalytic dehydrogenation of alkanes comprises: a reactor and a disengager, wherein the disengager is located above the reactor and is of an equal-diameter tank body structure. The reactor is of an equal-diameter cylindrical structure. The diameter of the reactor is smaller than that of the disengager. The stripping section below the reactor is a tapering section, the tapering section is connected with a spent catalyst conduit, and baffles is arranged in the tapering section.

A catalyst riser is arranged inside the reaction section, an outlet of the regenerated catalyst conduit is connected with the catalyst riser in the reactor. A rising medium pipe for conveying a rising medium is arranged in the catalyst riser. Both the reactor and the rising medium pipe are of cylindrical structures and are arranged coaxially. The bottom of the catalyst riser is closed, and the rising medium pipe extends into the riser through the bottom or side wall of the catalyst riser. An outlet end of the rising medium pipe and the highest point of an outlet of the regenerated catalyst conduit are nearby, and are optimally located in the same horizontal plane, or the outlet end of the rising medium pipe is slightly higher than the outlet of the regenerated catalyst conduit.

A feeding annular pipe is arranged in a lower portion of the reactor, and a spray nozzle is arranged on the annular pipe and faces downwards. Grilles or porous distribution plates are arranged in the reaction section and above the feeding annular pipe. The diameter of the disengager is greater than that of the reactor, and a ratio of the maximum diameter of the disengager to the diameter of the reactor is a range from 4/1 to 1.1/1.

The reaction device is combined with any catalyst regeneration device in the prior art. Herein, the structure of an adopted regeneration device and connection thereof are as follows:

the other end of the regenerated catalyst conduit and the other end of the spent catalyst conduit are respectively connected with a catalyst regeneration disengager and a regeneration section of the regeneration device, and the regeneration disengager of the regeneration device is located above the regeneration section. Spent catalyst from the reactor enters the tapering section from a lower part of the reaction section bed layer, is subjected to gas stripping by nitrogen or other gases not affecting the dehydrogenation reaction of the feed and then enters the regeneration section through the spent catalyst conduit.

An external circulating pipe is arranged between the regeneration disengager and the catalyst regeneration section, one end of the external circulating pipe is connected with a lower side part of the catalyst regeneration section, and the other end of the external circulating pipe is connected with a lower side part of the regeneration disengager.

A stand pipe is arranged on the regenerated catalyst conduit close to the regeneration disengager, and is a pipe parallel to an axial direction of the regeneration disengager. Herringbone baffles are arranged in the stand pipe.

Other arrangements in the disengager and the regeneration disengager are consistent with those in the present disclosure.

Experiment 1

Producing propene through dehydrogenation of propane by adopting equipment in the embodiment 1 of the present disclosure:

Feed: 99 wt % propane; feed rate: 0.6 t/h

Catalyst: environment-friendly metal oxide catalyst ADHO-1 (Referring to Chinese patent No. ZL 201110123675.1)

Reaction conditions: layers of grilles were arranged in the catalyst bed layer in the reaction reactor, and the distance of adjacent layers of grilles was 0.5 m; an average temperature of the bed layer was 600° C.; a pressure of the disengager was 0.03 MPa; a mass space-time is 3 h; an average linear speed of gas at a cross section of an outlet of the riser in the reactor was 0.5 m/s; and an average linear speed of gas at a cross section of a joint of the bottom of the disengager and the reactor was 2 m/s.

Regeneration conditions: layers of grilles were arranged in the dense-phase section of the regenerator, and the distance of adjacent layer of grilles was 0.5 m; and a temperature of the dense-phase section of the regenerator was 700° C.

Reaction-regeneration system: the present disclosure; Comparison device described as follows.

Reaction products obtained in the reaction-regeneration system of embodiment 1 were contrasted to that of embodiment 5 under the above the reaction conditions.

Comparison results are shown in Table 1:

TABLE 1

Product distribution and propene selectivity for dehydrogenation of 99 wt % propane, wt %

| Composition | the reaction-regeneration system of Embodiment 5 | | the reaction-regeneration system of Embodiment 1 | |
| --- | --- | --- | --- | --- |
| | Product distribution | Selectivity | Product distribution | Selectivity |
| $H_2$ | 1.55 | | 1.51 | |
| $CH_4$ | 1.74 | | 1.35 | |
| $C_2H_6$ | 1.35 | | 1.26 | |
| $C_2H_4$ | 1.16 | | 1.02 | |
| $C_3H_8$ | 60.43 | | 60.55 | |
| $C_3H_6$ | 32.28 | 83.69 | 33.62 | 87.44 |
| $C_4H_8$ | 0.45 | | 0.12 | |
| C5+ | 0.21 | | 0 | |
| Coke | 0.83 | | 0.57 | |

The results employing the devices of Embodiment 1 and Embodiment 5 were shown in the Table 1. It was shown that the single pass yield of propene obtained in the reaction device of the present disclosure was higher than that of the comparison scheme by 1.34%, the selectivity to propene was 3.75% higher, and the improvement effect was remarkable.

Experiment 2

Producing iso-butene through dehydrogenation of iso-butane by adopting equipment in the embodiment 1 of the present disclosure:

Feed: 98 wt % iso-butane; feed rate: 0.5 t/h.

Catalyst: environment-friendly metal oxide catalyst ADHO-1 (Referring to Chinese patent No. ZL 201110123675.1).

Reaction conditions: layers of grilles were arranged in the catalyst bed layer in the reaction reactor, and the distance of adjacent layers of grilles was 0.5 m; an average temperature of the bed layer was 580° C.; a pressure of the disengager was 0.025 MPa; a mass space-time was 3 h; an average linear speed of gas at a cross section of an outlet of the riser in a reactor was 0.45 m/s; and an average linear speed of gas at a cross section of a joint of the bottom of the disengager and the reactor was 1.8 m/s.

Regeneration conditions: layers of grilles were arranged in the dense-phase section of the regenerator, and the distance of adjacent layers of grilles was 0.5 m; and a temperature of the dense-phase section of the regenerator was 700° C.

Reaction products obtained in the reaction-regeneration system of embodiment 1 were contrasted to that in embodiment 5 under the above the reaction conditions.

TABLE 2

Product distribution and iso-butene selectivity
for dehydrogenation of 98 wt % iso-butane, wt %

| Composition | the reaction-regeneration system of Embodiment 5 | | the reaction-regeneration system of Embodiment 1 | |
|---|---|---|---|---|
| | Product distribution | Selectivity | Product distribution | Selectivity |
| $H_2$ | 1.64 | | 1.58 | |
| $CH_4$ | 1.65 | | 1.35 | |
| $C_2H_6$ | 0.55 | | 0.54 | |
| $C_2H_4$ | 0.48 | | 0.37 | |
| $C_3H_8$ | 0.79 | | 0.68 | |
| $C_3H_6$ | 1.1 | | 1.01 | |
| $i-C_4H_{10}$ | 46.74 | | 44.46 | |
| $n-C_4H_{10}$ | 1.85 | | 1.82 | |
| $n-C_4H_8$ | 1.46 | | 1.39 | |
| $i-C_4H_8$ | 41.46 | 80.88 | 45.28 | 84.57 |
| C5+ | 1.25 | | 0.77 | |
| Coke | 1.03 | | 0.75 | |

The results employing the devices of embodiment 1 and embodiment 5 were shown in the Table 2. It was shown that the single pass yield of propene obtained in the reaction device of the present disclosure was higher than that of the comparison scheme by 3.82%, the selectivity to iso-butene was 3.69% higher, and the improvement effect on the selectivity to iso-butene was very obvious.

Experiment 3

Pure butane was taken as feed for cracking, the reaction-regeneration device provided by the present disclosure was adopted, and the catalyst was non-noble-metal environment-friendly catalyst produced according to ZL 201110123675.1.

Nitrogen was adopted as a rising medium, an average temperature inside a reactor was 700° C., a reaction pressure (by hydrocarbon partial pressure) was 0.039 MPa, an average residence time of oil gas in a dense-phase section of the reactor was 5 s, a superficial gas velocity of oil gas in the dense-phase section under actual reaction conditions was 1.4 m/s, and a superficial gas velocity of oil gas in a dilute-phase section was 13 m/s. Product distribution was shown in Table 3.

Experimental 4

Mixed pentanes (55 wt % of n-pentane+45 wt % of iso-pentane) were taken as the feed for cracking, the reaction-regeneration device provided by the present disclosure was adopted, and the catalyst was non-noble-metal environment-friendly catalyst produced according to ZL 201110123675.1.

Nitrogen was adopted as a rising medium, an average temperature inside a reactor was 700° C., a reaction pressure (by hydrocarbon partial pressure) was 0.048 MPa, an average residence time of oil gas in a dense-phase section of the reactor was 3.5 s, a superficial gas velocity of oil gas in the dense-phase section under actual reaction conditions was 1.7 m/s, and a superficial gas velocity of oil gas in a dilute-phase section was 15 m/s. Product distribution was shown in Table 3.

TABLE 3

Dehydrogenation and cracking
product yield of experimental cases 3-4, wt %

| | Experiment 3 | Experiment 4 |
|---|---|---|
| Methane | 12.71 | 11.23 |
| Ethane | 3.8 | 6.68 |
| Ethene | 19.19 | 18.5 |
| Propane | 0.45 | 0.78 |
| Propene | 20.75 | 20.01 |
| Iso-butane | 0.03 | 0.02 |
| N-butane | 30.15 | 0.46 |
| Trans-2-butene | 0.98 | 1.52 |
| 1-butene | 1.24 | 2.81 |
| Iso-butene | 1.7 | 5.6 |
| Cis-2-butene | 0.45 | 1.14 |
| Iso-pentane | 0.21 | 9.65 |
| N-pentane | 0 | 12.84 |
| 1,3-butadiene | 2.59 | 2.32 |
| 3-methyl-1-butene | 0.1 | 0.1 |
| Trans-2-pentene | 0.1 | 0.18 |
| Pentene | 0.15 | 0.22 |
| 2-methyl-2-butene | 0.09 | 0.3 |
| Cis-2-pentene | 0 | 0.28 |
| C6+ | 1.53 | 0.96 |
| Hydrogen | 0.51 | 0.75 |
| Coke | 3.27 | 3.65 |

Experiment 5

Pure butane was taken as the feed for cracking, pure propane was taken as the feed for dehydrogenation, and a feed mass ratio of the pure butane to the pure propane was 1:2. The catalyst was non-noble-metal environment-friendly catalyst produced according to ZL 201110123675.1. The catalyst was also adopted in the experiments 6 and 7.

An average temperature of a cracking area was 700° C., an average residence time of oil gas in the cracking area was 5 s, and a superficial gas velocity of oil gas in the cracking area under actual reaction conditions was 1.7 m/s.

An average temperature of a dehydrogenation area was 600° C., a pressure of a disengager (by hydrocarbon partial pressure) was 0.042 MPa, an average residence time of oil gas (including oil gas product by cracking) in the dehydrogenation area was 8 s, and a superficial gas velocity of oil gas was 1.0 m/s in the dehydrogenation area under actual reaction conditions. Product distribution was shown in Table 4.

Experiment 6

Pure butane was taken as feed for cracking, pure iso-butane was taken as the feed for dehydrogenation, and a feed mass ratio of pure butane to pure iso-butane was 1:2.

An average temperature of a cracking area was 700° C., an average residence time of oil gas in the cracking area was 4 s, and a superficial gas velocity of the oil gas was 1.8 m/s in the cracking area under actual reaction conditions.

An average temperature of a dehydrogenation area was 580° C., a pressure of a disengager (by hydrocarbon partial pressure) was 0.044 MPa, an average residence time of oil gas (including oil gas product by cracking) was 7 s in the dehydrogenation area, and a superficial gas velocity of oil gas was 0.8 m/s in the dehydrogenation area under actual reaction conditions. Product distribution was shown in Table 4.

Experiment 7

Mixed pentanes (55 wt % of n-pentane+45 wt % of iso-pentane) were taken as feed for cracking, pure propane was taken as feed for dehydrogenation, and a feed mass ratio of mixed pentanes to pure propane was 1:2.

An average temperature of a cracking area was 690° C., an average residence time of oil gas in the cracking area was 4.5 s, and a superficial gas velocity of oil gas was 1.7 m/s in the cracking area under actual reaction conditions.

An average temperature of a dehydrogenation area was 600° C., a pressure of a disengager (by hydrocarbon partial pressure) was 0.048 MPa, an average residence time of oil gas (including oil gas product by cracking) was 8 s in the dehydrogenation area, and a superficial gas velocity of the oil gas was 1.0 m/s in the dehydrogenation area under actual reaction conditions. Product distribution was shown in Table 4.

TABLE 4

Dehydrogenation and cracking product yield of experiments 5-7, wt %

|  | Experiment 5 | Experiment 6 | Experiment 7 |
|---|---|---|---|
| Methane | 5.25 | 4.56 | 4.76 |
| Ethane | 1.95 | 1.30 | 2.91 |
| Ethene | 7.06 | 6.45 | 6.83 |
| Propane | 40.44 | 0.30 | 40.55 |
| Propene | 28.40 | 8.59 | 27.22 |
| Iso-butane | 0.01 | 31.48 | 0.01 |
| N-butane | 6.52 | 6.71 | 0.15 |
| Trans-2-butene | 1.26 | 1.69 | 0.51 |
| 1-butene | 1.24 | 1.55 | 0.94 |
| Iso-butene | 0.70 | 30.06 | 1.87 |
| Cis-2-butene | 0.87 | 1.18 | 0.39 |
| Iso-pentane | 0.21 | 0.07 | 3.36 |
| N-pentane | 0.00 | 0.00 | 4.28 |
| 1,3-butadiene | 0.89 | 0.90 | 0.80 |
| 3-methyl-1-butene | 0.03 | 0.03 | 0.03 |
| Trans-2-pentene | 0.03 | 0.03 | 0.06 |
| Pentene | 0.05 | 0.05 | 0.07 |
| 2-methyl-2-butene | 0.03 | 0.03 | 0.10 |
| Cis-2-pentene | 0.00 | 0.00 | 0.09 |
| C6+ | 0.51 | 1.60 | 0.32 |
| Hydrogen | 0.92 | 1.39 | 1.00 |
| Coke | 3.61 | 2.02 | 3.74 |

Experiment 8

The inverted-conical frustum-shaped regenerator (i.e., diameters of cross sections of the regenerator gradually increase from bottom to top) provided by the present disclosure was adopted. A dense-phase bed layer had a height of 8 m, a superficial gas velocity in the bottom of the dense-phase bed layer was 0.8 m/s, a superficial gas velocity in the top of the dense-phase bed layer was 0.1 m/s, and no sleeve was arranged at the bottom of the bed layer. A ratio of air to natural gas was determined with excess oxygen of 2 vol % based on complete combustion of natural gas. A catalyst dense-phase bed layer had a bottom temperature of 680° C. and a top temperature of 705° C., and a temperature in the dilute-phase of the regenerator was 713° C. The content of CO in flue was 0.35 vol %.

Experiment 9

The inverted-conical frustum-shaped regenerator (i.e., diameters of cross sections of the regenerator gradually increase from bottom to top) provided by the present disclosure was adopted. A dense-phase bed layer had a height of 8 m, a superficial gas velocity in the bottom of the dense-phase bed layer was 0.8 m/s, and a superficial gas velocity in the top of the dense-phase bed layer was 0.1 m/s.

A sleeve was arranged at the bottom of the bed layer and has a height of 2 m, and an internal average superficial gas velocity of the sleeve was 4 m/s. A ratio of air to natural gas was determined with excess oxygen of 2 vol % based on complete combustion calculation of natural gas. Under such conditions, a catalyst dense-phase bed layer had a bottom temperature of 693° C. and a top temperature of 701° C., and a temperature in the dilute-phase of the regenerator was 707° C. The content of CO in flue was 0.12 vol %.

Obviously, the sleeve was more beneficial to full combustion of fuels, promoted the internal circulation of catalyst and further improved temperature distribution.

The invention claimed is:

1. A catalyst regeneration device, comprising
a regenerator for accommodating a catalyst and a regeneration disengager,
wherein diameters of cross sections of the regenerator are decreased from top to bottom, and
a circular pipe sleeve is arranged at a lower position inside the regenerator.

2. The catalyst regeneration device according to claim 1, wherein the circular pipe sleeve is parallel to an axis of the regenerator.

3. The catalyst regeneration device according to claim 1, wherein the circular pipe sleeve is coaxial with the regenerator.

4. The catalyst regeneration device according to claim 1, wherein a height of the circular pipe sleeve in the regenerator is less than two thirds of a height of a catalyst dense-phase bed layer.

5. The catalyst regeneration device according to claim 1, wherein a height of the circular pipe sleeve in the regenerator is less than one third of a height of a catalyst dense-phase bed layer.

6. The catalyst regeneration device according to claim 1, wherein, fuel and air are directly fed into the circular pipe sleeve.

7. A regeneration method for alkane dehydrogenation catalyst, comprising the following step:
spent catalyst entering a regeneration disengager, and fuel and air entering a regenerator from a lower part or bottom of the regenerator;
gas moving upwards in the regenerator, a linear speed of the gas gradually decreasing from bottom to top, and, the spent catalyst moving upwards at a central area and moving downwards at a side wall area in the regenerator so as to form an internal circulation; and
a regenerated catalyst leaving the regenerator through a regenerated catalyst conduit, and the flue resulting from a combustion reaction being discharged from a flue outlet in a top of the regeneration disengager.

8. The regeneration method according to claim 7, wherein a circular pipe sleeve is arranged in the lower part of the regenerator, and fuel and air enter the circular pipe sleeve from a lower part or bottom of the regenerator.

9. The regeneration method according to claim 8, wherein a superficial gas velocity inside the circular pipe sleeve is in a range from 1 m/s to 30 m/s.

10. The regeneration method according to claim 7, wherein a superficial gas velocity inside the circular pipe sleeve is in a range from 3 m/s to 5 m/s.

11. The regeneration method according to claim 7, wherein a superficial gas velocity of a bottom fuel inlet of a catalyst dense-phase bed layer of the regenerator is in a range from 0.1 m/s to 3 m/s under actual operating conditions.

12. The regeneration method according to claim 7, wherein a superficial gas velocity of a bottom fuel inlet of a catalyst dense-phase bed layer of the regenerator is in a range from 0.3 m/s to 2 m/s under actual operating conditions.

13. The regeneration method according to claim 7, wherein a temperature inside the regenerator is 600° C. to 850° C.

14. The regeneration method according to claim 7, wherein a temperature inside the regenerator is 630° C. to 750° C.

* * * * *